United States Patent [19]

Langdon

[11] Patent Number: 4,956,635
[45] Date of Patent: Sep. 11, 1990

[54] METHOD AND APPARATUS FOR TESTING PERSONAL BARRIERS

[76] Inventor: Robert S. Langdon, 29 Beaver La., Bedford, N.H. 03102

[21] Appl. No.: 339,129

[22] Filed: Apr. 14, 1989

[51] Int. Cl.$^5$ .............................................. G08B 21/00
[52] U.S. Cl. ....................................... 340/540; 606/34
[58] Field of Search ............................... 340/540, 647;
128/303.13; 361/220, 232, 42, 49; 174/558, 556;
606/35, 34

[56] References Cited

U.S. PATENT DOCUMENTS

| | | | |
|---|---|---|---|
| 4,206,631 | 6/1980 | Nysse et al. | 73/40 |
| 4,321,925 | 3/1982 | Hoborn et al. | 361/224 |
| 4,799,384 | 1/1989 | Casali | 73/45.5 |

FOREIGN PATENT DOCUMENTS

| | | | |
|---|---|---|---|
| 2208300 | 6/1974 | France | 340/540 |
| 0712082 | 1/1980 | U.S.S.R. | 128/303.13 |

Primary Examiner—Joseph A. Orsino
Assistant Examiner—Geoff Sutcliffe
Attorney, Agent, or Firm—Davis, Bujold & Streck

[57] ABSTRACT

The method and apparatus for testing a personal barrier such as a medical glove comprises establishing a reference circuit through the body of an individual wearing the personal barrier. An electrical lead is connected with a saline solution or the body of the patient. The defective personal barrier is indentified through the establishment of an external circuit through the practitioner and the test solution or the patient. An alarm is sounded to alert the wearer to the defective condition. The detection is preferably accomplished by means of sensing the resistance of the external circuits.

16 Claims, 3 Drawing Sheets

METHOD AND APPARATUS FOR TESTING PERSONAL BARRIERS

BACKGROUND OF THE INVENTION

(1) Field of the Invention

The present invention relates generally to improved methods and apparatus for testing protective clothing such as gloves and other personal barriers used by health care providers and others who handle hazardous materials. More particularly, the present invention relates generally to methods and apparatus for testing medical gloves to identify defective holes or rips therein. Accordingly, the present invention is directed to novel and improved methods and devices of such character.

(2) Prior Art and General Background

One of the most critical current health concerns is the transmission of contagious diseases, such as the AIDS virus and the hepatitis B virus as well as other infectious diseases, through inadvertent direct contact. Such concerns have been heightened in the health provider population wherein health care professionals are routinely potentially exposed to such diseases during the performance of their duties and, in fact, have in some cases contracted such highly disabling and life threatening diseases through direct body contact. Usage of "rubber" examination and surgical gloves has represented the primary barrier to direct contact with the AIDS and hepatitis viruses. However, one of the drawbacks to the use of "rubber" gloves resides in the fact that the integrity of the glove is usually not evident on routine visual inspection. In particular, a number of studies have shown that a substantially large percentage of latex gloves, both surgical and examination, have pores of sufficient magnitude to allow for direct communication of potentially infectious agents through the gloves. In some studies, nearly thirty percent (30%) of all of the medical gloves tested were found to have impermissibly large openings.

Latex examination and surgical gloves are conventionally tested for quality pursuant to a number of testing standards developed by the American Society of Testing and Materials. For example, examination gloves are tested by filling the glove with approximately 300 milliliters of water at room temperature and observing the glove in a vertical position for a period of time, such as, typically, a minimum of two minutes. The emergence of water from the glove signals a failure of the glove. The minimum thickness for the typical rubber examination glove is 0.08 mm.

Latex surgical gloves, which are ordinarily employed in operating rooms, are tested by fastening the cuff of the glove to a circular mandrel. The glove is inflated with air pressure to a gage pressure of 1.5 kPa and the inflated glove is then immersed in water at room temperature to a depth of pf 200± 10 mm above the tip of the middle finger. The immersion time is typically on the order of 1.5 minutes. The emergence of air bubbles from the glove is a signal of failure.

The adoption and implementation of glove testing standards has not resulted in the widespread proliferation of defect-free gloves for the medical professions. Additionally, a major deficiency of the above-discussed techniques for testing either rubber examination gloves or rubber surgical gloves is that the tests are time specific and neither account for or test for any subsequent emergence or formation of a defective hole or a tear in the glove. The presence of even statistically small numbers of defective gloves can result in very ominous consequences to the medical professions.

While the state of the art has been discussed above in the context of medical gloves, and the invention will be described below primarily in this context, it is to be understood that similar problems are presented by other medical apparel, such as surgical gowns, and by clothing used in the waste disposal field.

SUMMARY OF THE INVENTION

Briefly stated, the invention in a preferred form is a method for testing the integrity of personal barriers such as conventional medical gloves which are routinely used by health professionals. The invention also encompasses a method and apparatus for continuously testing such personal barriers to determine whether or not the barrier remains in a safe condition during its intended use.

The method comprises establishing a reference external electrical circuit connecting two regions of the body of a health professional. The existence of the thus established reference electrical circuit is continuously verified. A status signal indicative of the verification is generated. The status signal is monitored by the health professional. Electrical communication is also established between the body of the health professional and a test point. A determination is made as to whether a second external circuit is formed between the professional and the test point. An alarm signal indicative of the detection of such an external electrical circuit is generated, thereby signaling a defective glove or the like.

The alarm signal may be communicated both by illuminating a light device and sounding an acoustical alarm. The reference external electrical circuit may be established by the health professional stepping on a mat. The testing method comprises, in one embodiment, establishing electrical communication with a saline solution and inserting the donned glove in the solution to determine whether an external electrical circuit is formed between the health professional and the solution. In another embodiment of the testing method, electrical communication is established with the body of the patient. The verification step may be accomplished by determining whether the resistance of the reference external circuit lies within a pre-established range. Detection of the external testing circuit may also be accomplished by determining whether the external resistance of the second external circuit lies within a pre-established range.

An apparatus for testing the integrity of a medical glove in accordance with the present invention comprises a reference circuit which includes first and second terminals for establishing an external reference circuit traversing a portion of the body of a health professional. A test circuit includes a third terminal for establishing an external test circuit between the first terminal and the third terminal in the event of a glove defect. Detection circuitry continuously verifies the existence of the external reference circuit. A status signal verifies the detection of the external reference circuit. Detection circuitry also detects the existence of the external test circuit. An alarm signals the detection of the external test circuit to identify a defective glove.

The verification circuitry includes a comparator for comparing the detected resistance of the reference circuit to a pre-established resistance range. The status signal preferably comprises a light emitting diode which emits a continuous series of discrete flashes. The detection circuitry includes a second comparator which compares the detected resistance of the test circuit with a pre-established range. The alarm preferably comprises an acoustical alarm and a visual indicator. A mat may be provided to electrically communicate with the first and second terminals to facilitate establishment of the reference circuit.

An object of the invention is to provide a new and improved method and apparatus for testing personal barriers used in medical or waste disposal applications.

Another object of the invention is to provide a new and improved method and apparatus for monitoring the integrity of "rubber" gloves and/or protective gowns while the gloves/gown are used during a medical procedure.

A further object of the invention is to provide a new and improved method and apparatus for testing gloves which is highly reliable and is accomplished in an efficient and cost effective manner.

A yet further object of the invention is to provide a new and improved method and apparatus for testing gloves which may be employed to identify a defective glove at substantially the moment that the defect arises.

Other objects and advantages of the invention will become apparent from the drawings and the specification.

DETAILED DESCRIPTION OF THE INVENTION

Figure 1:
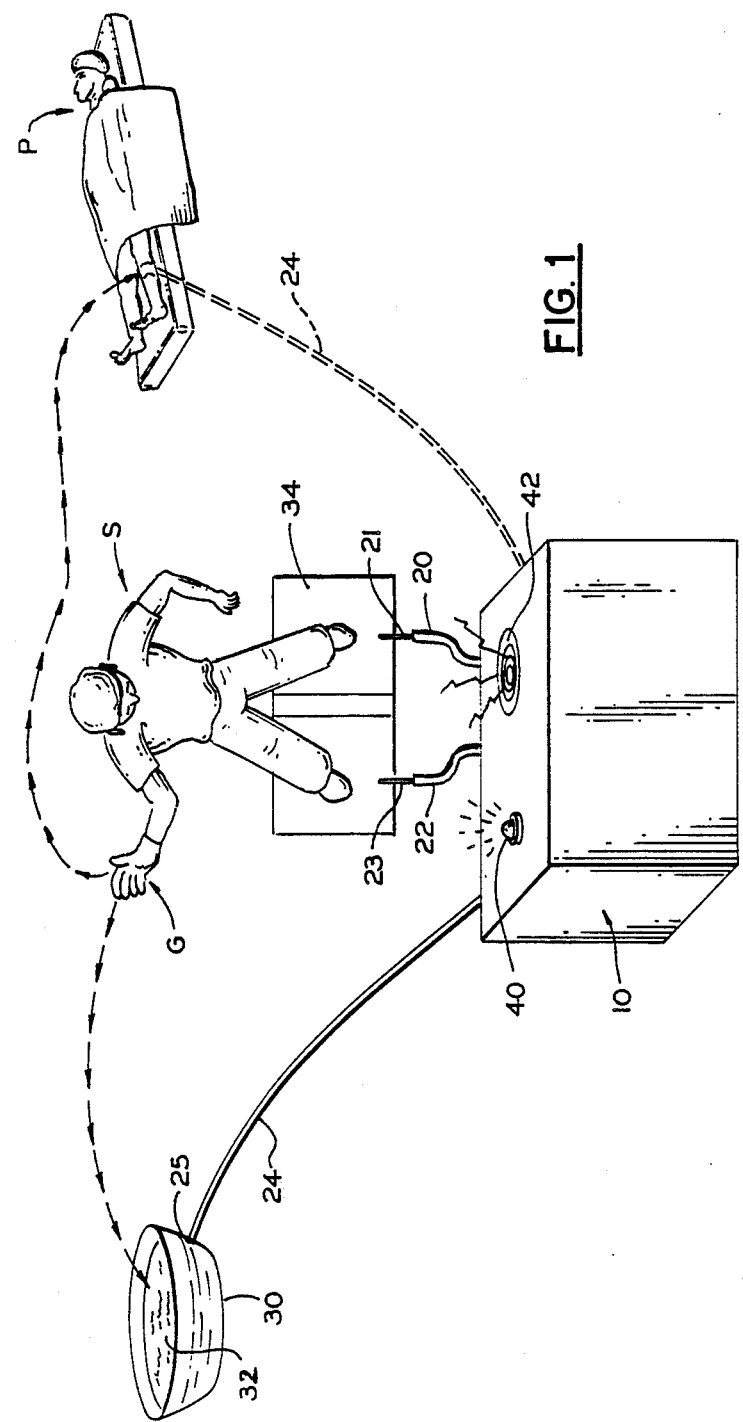
FIG. 1 is a schematic view illustrating the method and apparatus for testing a glove in accordance with the present invention.

With reference to the drawings, wherein like numerals represent like parts in the figures, the invention employs a personal barrier tester designated generally by the numeral 10. The tester 10 functions to continuously test an examination or surgical glove before and during usage as will be described hereinafter. Although not limited in application, the invention is particularly useful in connection with detecting glove defects as may arise or occur in the course of health or medical applications. The tester 10 regularly alerts the health professional as to the proper ongoing operation of the tester and also promptly signals an alarm in the event that a defect in the glove has been detected.

The tester 10 has at least three electrical probes or leads 20, 22, and 24 which provide electrical connections to form external circuits as will be described below. The probes preferably respectively terminate in conventional EKG-type electrodes 21, 23 and 25. The testing and monitoring is efficiently accomplished at different glove usage stages.

The glove is tested for defects prior to initial usage and is also continuously tested for defects while being used. The invention encompasses simultaneous testing for a pair of gloves. However, for purposes of clarity, the invention will essentially be described in terms of a single glove G. The glove G to be tested may be used by anyone and, in particular, health professionals such as physicians, nurses, surgeons, dentists and the like. For purposes of illustration, the invention will be described in relation to a surgeon S. In a pre-glove usage stage, probes 20 and 22 are connected to the surgeon S in a manner similar to the connection of EKG electrodes to a patient. The electrical connection of probes 20 and 22 may, alternatively, be accomplished by the surgeon S standing on appropriate right foot and left foot locations of a mat 34 to which the probes are electrically connected by, for example, conductive plastic strips integral with the surgeons boots. When the surgeon is properly standing on the right and left foot pads of the mat 34, or the electrodes are otherwise properly attached to the surgeon S, an indicator light 40 will intermittently flash on and off in a series of discrete flashes. The indicator light thereby indicates that the tester 10 is properly connected to the surgeon S and the tester is operating in a proper manner.

Probe 24 is connected to a stainless steel basin 30. Basin 30 is a conventional basin used in medical applications and operating rooms. A saline solution 32 is placed in the basin 30. After the surgeon S is dressed and the glove G donned, the glove G is initially tested by placing the gloved hand into the sterile saline solution 32 in bowl 30. In the event that there is a defect in the glove, an external circuit will be established through the glove. The flashing indicator light 40 will accordingly transform to a constant illuminated mode and an acoustical alarm 42 will be sounded. Alarm 42 may be in the form of a buzzer. The indicator 40 and alarm 42 produce positive signals that a hole or tear in the glove has been detected. The glove G may then be removed and changed and the test repeated until a non-defective glove is identified.

When the surgical procedure or examination is commenced, the electrode 25 is disconnected from the stainless steel bowl 30 and attached to the patient P. The surgeon S may either stand on a mat 34 or, where more mobility is desired, the probes may be directly attached to the surgeon's body. The probe leads may dangle out from underneath the gown of the surgeon and are sufficiently long to allow relatively free movement of the surgeon. The surgeon then carries out the desired procedure in a conventional manner while from time-to-time monitoring the tester 10 to be sure the light 40 is flashing.

The tester 10 continuously produces an intermittent flashing light pattern via the indicator light 40 if the device is operating properly. In the event that a hole or a rip occurs in the glove G, or a current flow path is otherwise established between the surgeon and the patient, the indicator light 40 will immediately transform to a constant illumination and the audible alarm 42 will be energized. The tester 10 essentially functions by establishing an external reference circuit through the surgeon, and in the event of a defective glove, a second external circuit between the surgeon and the patient or, alternatively, the surgeon and the saline solution contained in the bowl. A non-defective glove functions as an electrical insulator to prevent the completion of the electrical circuit through the patient and the surgeon. If there are holes in any of the gloves, including holes which would not be detected by the above-described prior testing procedures, the external circuit will be completed and the holes will be immediately detected.

Figure 2:
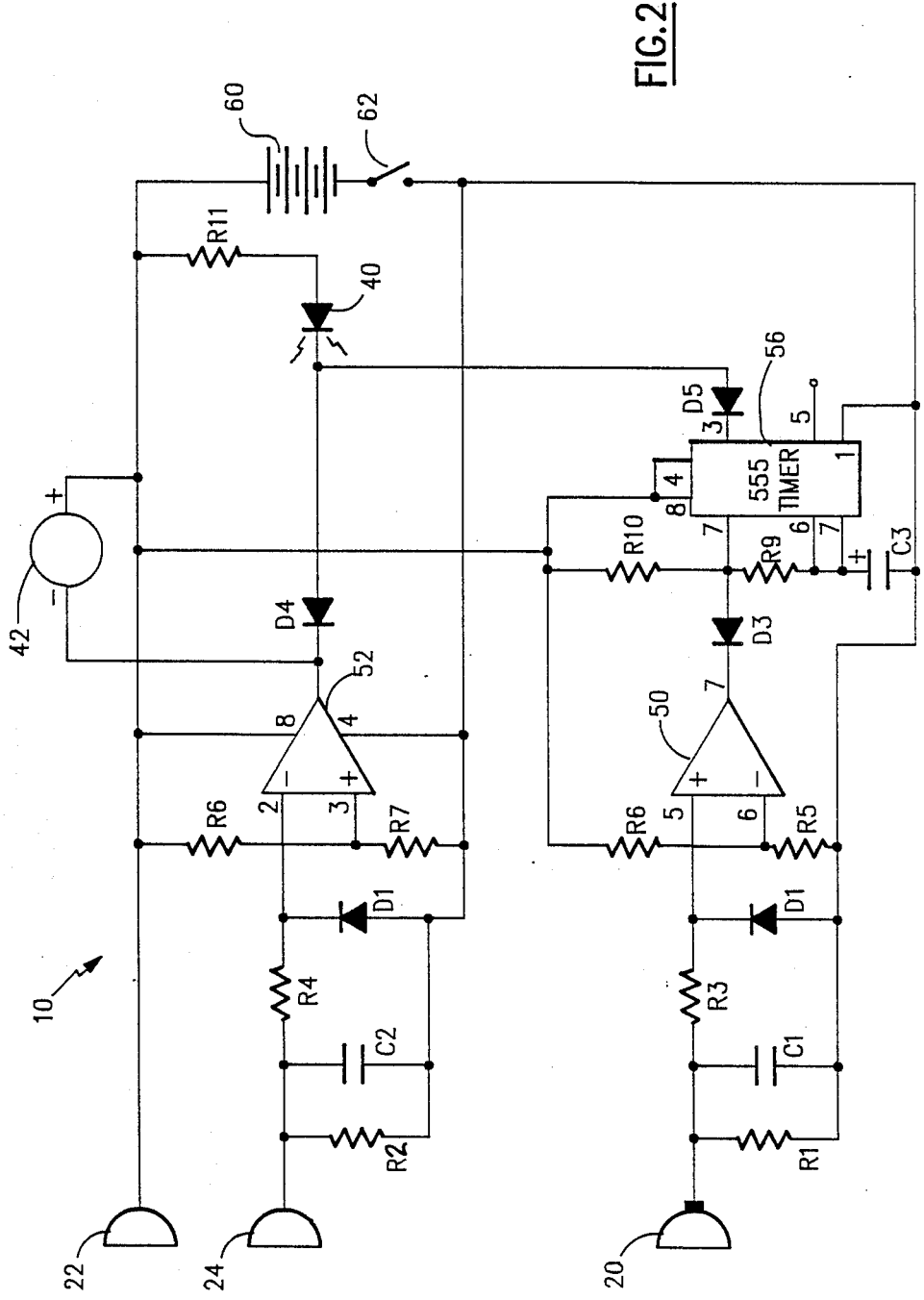
FIG. 2 is a schematic diagram of an electrical circuit which may be employed in the apparatus of the present invention.

The glove tester circuitry for a preferred embodiment is illustrated in FIG. 2. The tester 10 employs a pair of comparators 50 and 52, and a 555-type timer integrated circuit 56 to generate output signals which are applied to the LED 40 and an audible alarm 42. Power for the tester is supplied via a battery 60. In preferred form, the battery is a 5.6 volt air activated battery which produces a constant current of approximately 5.0 milliamps. An on/off switch 62 may be employed, but is optional. During operation of the tester, the current flow through the circuit comprising the probes 20 and 22 and probes 22 and 24 is not greater than approximately 0.00000054 amperes.

With additional reference to FIG. 2, resistors R1 and R2 are employed to define the input resistance for the tester operates, i.e., the maximum external circuit resistance to which the device is responsive. Ordinarily, the tester is employed to test for resistances of from 0 ohms to 10 megohms. Filter capacitors C1 and C2 function to filter out currents commensurate with stray electromagnetic radiation, including the 60 hertz radiation which may be generated by fluorescent lights and other radiating electrical devices, which may result from voltages induced in the probes. Resistors R3 and R4 are current limiting resistors which protect the comparators 50 and 52 in the event of a short circuit across a pair of probes. Diodes D1 and D2 function to prevent the input voltage to each of the comparators 50 and 52 from going negative. Resistors R5 and R6 set the bias voltage at the negative input of comparator 50, and resistors R7 and R8 set the bias voltage at the positive input of comparator 52.

Comparator 50 normally provides a negative output which is reflected to pin 7 of the timer thus clamping the timer in the off position, i.e., compacitor C3 will not charge via resistors R9 and R10 so long as the output of comparator 50 is low. A resistance between probes 20 and 22 in the range of from 0 to 10 megohms (in the preferred embodiment and preferred application) will cause the output of comparator 50 to go high. Likewise, a resistance in the range of 0 to 10 megohms between probes 22 and 24 will result in the output of comparator 52, which is normally high going low. The comparators are biased so as to be non-responsive above the 10 megohm range. As noted above, in the event that the external resistance between probes 20 and 22 is lower than 10 megohms, which is the normal operating condition, the output of comparator 50 will go high and capacitor C3 will change thus starting the timer. The output frequency of timer 56 is established by the RC time constant of the circuit comprising capacitor C3 and resistors R9 and R10. The output pin 3 of timer 56 pulses high and low when the timer is operating. When the output signal on pin 3 is high, the LED 40 is extinguished. When the output signal on timer pin 3 is low, the timer completes a path for current flow from battery 60 through the LED and LED 40 is thus energized by battery 60 via resistor R11 and flashes. The flashing LED 40 provides a visual indication that the continuity between the external circuit from probe 20 to probe 22 is within the expected pre-established resistance range, typically, 0 to 10 megohms, and the tester is properly operating.

If the output of comparator 52 switches from positive to negative, indicating that the external resistance in the input circuit to the comparator has fallen below 10 megohms, a current flow path which includes LED 40 will be completed through the capacitor. This will result in LED 40 being continuously on and the audible alarm 42 being activated. Any openings through glove G will result in its ceasing to be an insulator and its becoming a resistance in parallel with R2. The value of this resistance will be a function of the area of the opening.

The glove tester 10, as described, has been employed in connection with testing surgical gloves having a minimum wall thickness on the order of 0.10 mm. The glove tester has been found to identify failed gloves with sufficient sensitivity so that the precise finger and position of the hole could be determined. One test of the glove tester and the testing method in accordance with the present invention was conducted in an operating room environment. There was found to be no interference with or by the function and the use of electronic diagnostic equipment such as EKG monitors, blood oximeters and electric temperature and pulse monitors. There was found to be no discharge or transmission of RF current to the physician/nurse using the tester when a cautery device was set at 400 watts output. It was also noted that the monitors and other devices did not interfere with the function of the tester. The current emitted to the physician and patient to which the glove tester was employed was no greater than 0.00000054 amps. It should be noted that the tester employs a direct current and is essentially isolated from other electrical devices.

Figure 3:
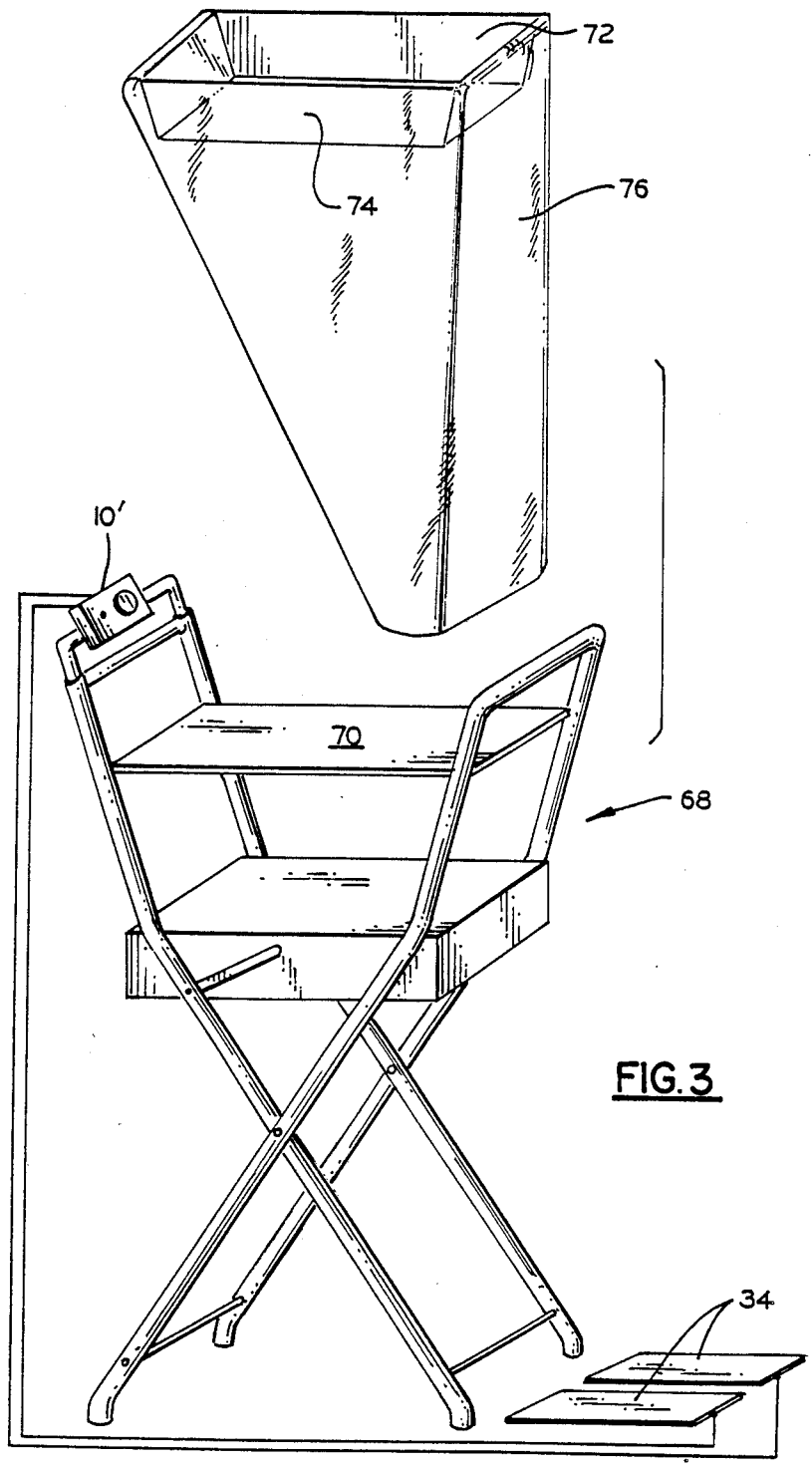
FIG. 3 is a perspective view of a basin holder which may be employed as part of a test system in accordance with the present invention.

Referring to FIG. 3, if a defect in a glove occurs during a surgical procedure, the surgeon may wish to test the replacement glove before continuing with the procedure. In such case, he will return to the basin 30. How at this time the surgeon's gown will be sterile and would be capable of being contaminated by the stand on which the basin is supported. In accordance with the invention, a stand 68 is provided which has a built-in tester 10' and a conductive platform 70 which will support a disposable plastic basin 72 having an electrode 74 extending therethrough to establish a current path from the tester 10, to the saline solution via the platform 70. The disposable plastic basin will be provided with an integral drape 76 which covers all parts of the stand which might come in contact with sterile clothing worn by the surgeon.

While a preferred embodiment of the foregoing invention has been set forth for purposes of illustration, the foregoing description should not be deemed a limitation of the invention herein. Accordingly, various modifications, adaptations, and alternatives may occur to one skilled in the art without departing from the spirit and scope of the invention.

What is claimed is:

1. A method for testing the integrity of a personal barrier worn by a human such as a health professional and the like comprising:
    (a) establishing a reference external electrical circuit connecting two regions of said human;
    (b) continuously verifying the existence of said reference electrical circuit;
    (c) generating a status signal indicative of said existence;
    (d) monitoring the status signal;
    (e) applying a personal barrier to the said human;
    (f) establishing electrical communication between a body and a test point;
    (g) determining whether a further external electrical circuit, indicating lack of the integrity of the personal barrier, is formed between at least one of said two regions of said human and said test point through said body and said personal barrier when only said personal barrier is in contact with said body; and (h) generating an alarm signal indicative of the existence of said further external electrical circuit between said human and said test point and of said lack of integrity of the personal barrier.

2. The testing method of claim 1 wherein said alarm signal comprises both visual and acoustical signals.

3. The testing method of claim 1 wherein step (a) comprises the human stepping on electrically conductive mat means.

4. The testing method of claim 1 wherein step (c) further comprises intermittently illuminating a light emitting diode.

5. The testing method of claim 1 wherein said body comprises a saline solution and step (g) comprises inserting the personal barrier at least partially in said solution to determine whether an electrical circuit is formed between said human and said solution transgressing the personal barrier.

6. The testing method of claim 1 wherein said body of step (f) is the body of a patient.

7. The testing method of claim 1 wherein step (b) comprises determining whether the external resistance of said reference external current lies within a pre-established range.

8. The testing method of claim 1 wherein step (g) comprises determining whether the external resistance of said further external electrical circuit lies within a preestablished range.

9. Apparatus for testing the integrity of a personal barrier worn by a human comprising:
reference circuit means comprising first and second terminal means for establishing a reference external circuit traversing a portion of a human between said first and second terminal means;
test circuit means comprising third terminal means for establishing a test external circuit between said first and third terminal means;
verification means for continuously verifying the presence of the reference external circuit;
status signal means responsive to said verification means for signaling the verification of said reference external circuit;
detection means for detecting the existence of a conductive path connecting said first terminal and said third terminal through the human and the personal barrier thereby indicating a lack of integrity of the personal barrier; and
alarm means responsive to said detection means for signaling the existence of said conductive path and the lack of the integrity of the personal barrier.

10. The test apparatus of claim 9 further comprising means for sensing the resistance of said reference external circuit and comparator means for comparing the reference resistance to a pre-established resistance range.

11. The test apparatus of claim 9 wherein said status signal means comprises a light emitting diode.

12. The test apparatus of claim 9 further comprising means for sensing the resistance of said conductive path and comparator means for comparing the resistance to a pre-established range.

13. The test apparatus of claim 9 wherein said alarm means comprises an acoustical alarm and a visual indicator.

14. The test apparatus of claim 9 further comprising electrically conductive mat means for establishing electrical communication between said human and said first and second terminal means.

15. The test apparatus of claim 9 wherein the test circuit means comprises:
a support stand including a platform being at least in part conductive;
basin means being supported on said platform for containing a conductive solution, said basin means having a conductive portion which establishes a current path between said platform and the solution when contained therein to form said third terminal;
drape means attached to said basin means about the periphery thereof, said drape means extending substantially entirely about the portions of said stand disposed below said platform; and
means for sensing for the presence of a path of electrical current flow between said platform and said human wearing said personal barrier when said personal barrier is at least partly immersed in the solution contained in said basin means.

16. The apparatus of claim 15 wherein said means for sensing includes:
mat means positioned adjacent said stand and including at least an electrically conductive portion; and
means for establishing an electrical contact between said human and said mat means electrically conductive portion.

* * * * *